US006462188B1

(12) United States Patent
Kirkness

(10) Patent No.: US 6,462,188 B1
(45) Date of Patent: Oct. 8, 2002

(54) HUMAN 5-HT3 RECEPTOR

(75) Inventor: Ewen F. Kirkness, Olney, MD (US)

(73) Assignee: The Institute for Genomic Research, Rockville, MD (US)

( * ) Notice: Subject to any disclaimer, the term of this patent is extended or adjusted under 35 U.S.C. 154(b) by 0 days.

(21) Appl. No.: 09/061,154

(22) Filed: Apr. 16, 1998

(51) Int. Cl.$^7$ .......................... C07H 21/04; C12N 1/20; C07K 1/00; A16K 38/00; G01N 33/566
(52) U.S. Cl. ..................... 536/23.5; 435/6; 435/7.2; 435/7.21; 435/69.1; 435/252.3; 435/325; 435/254.11; 435/320.1; 436/501; 530/350; 514/2; 536/23.1
(58) Field of Search .............................. 536/23.5, 23.1; 530/350; 436/501; 435/6, 7.2, 7.21, 69.1, 257.3; 514/2

(56) References Cited

U.S. PATENT DOCUMENTS 5,155,218 A    10/1992    Weinshank et al.

OTHER PUBLICATIONS

Belelli et al. Molecular Pharmacology 48:1054, 1995.*
Lankiewicz et al., Mol. Pharm. 53:202, 1998.*
Bowie et al., Science 247:1306, 1990.*
Maricq, A.V., et al., "Primary Structure and Functional Expression of the 5HT$_3$ Receptor, a Serotonin–Gated Ion Channel," *Science* (Oct. 18, 1991) 254:432–437.
Belelli, D., et al., "Cloning and Functional Expression of a Human 5–Hydroxytryptamine Type 3A$_s$ Receptor Subunit," *Molecular Pharmacology* (1995) 48:1054–1062.
Lankiewicz, S., et al., "Molecular Cloning, Functional Expression, and Pharmacological Characterization of 5–Hydroxytryptamine$_3$ Receptor cDNA and Its Splice Variants from Guinea Pig," *Molecular Pharmacology* (1998) 53:202–212.
Bonhaus, D.W., et al., "Pharmacological Characterization of 5–Hydroxytryptamine$_3$ Receptors in Murine Brain and Ileum Using the Novel Radioligand [$^3$H]RS–42358–197: Evidence for Receptor Heterogeneity," *Journal of Neurochemistry* (1993) 61(5):1927–1932.

Van Hooft, J. A., et al., "Native Serotonin 5–HT$_3$ Receptors Expressed in Xenopus Oocytes Differ from Homopentameric 5–HT$_3$ Receptors," *Journal of Neurochemistry* (1997) 69(3):1318–1321.

Hussy, N., et al., "Functional properties of a cloned 5–hydroxytryptamine ionotropic receptor subunit: comparison with native mouse receptors," *Journal of Physiology* (1994) 481.2:311–323.

Apud, J.A., "The 5–HT$_3$ Receptor in Mammalian Brain: A New Target for the Development of Psychotropic Drugs?" *Neuropsychopharmacology* (1993) 8(2):117–130.

Gralla, R.J., et al., "Antiemetic Efficacy of High–Dose Metoclopramide: Randomized Trials with Placebo and Prochlorperazine in Patients with Chemotherapy–Induced Nausea and Vomiting," *The New England Journal of Medicine* (Oct. 15, 1981) 305(16):905–909.

Rodgers, R.J., et al., "Profile of action of 5–HT$_3$ receptor antagonists, ondansetron and WAY 100289, in the elevated plus–maze test of anxiety of mice," *Psychopharmacology* (1995) 117:306–312.

Costall, B., et al., "The Antipsychotic Potential of GR$_{38032}$F, a Selective Antagonist of 5HT$_3$ Receptors in the Central Nervous System," *British Journal of Pharmacology* (Mar. 1987) 90:89P, Proceedings Supplement.

Zoldan, J., et al., "Ondansetron for hallucinosis in advanced Parkinson's disease," *The Lancet* (Feb. 27, 1993) 341:562–563.

* cited by examiner

Primary Examiner—Elizabeth Kemmerer
Assistant Examiner—Michael Brannock
(74) Attorney, Agent, or Firm—Morrison & Foerster LLP

(57) ABSTRACT

Recombinant materials for preparation of a new form of human 5-HT3 receptor are provided. These materials permit the production of said receptor, display of said receptor on host cells, and compositions of diagnostic and therapeutic utility.

14 Claims, 2 Drawing Sheets

Polypeptide sequence of human 5-HT3B (Serine 129) (SEQ ID NO:2)

MLSSVMAPLWACILVAAGILATDTHHPQDSALYHLSKQLLQKYHKEVRPVYNWTKATTVYLDLFVH
AILDVDAENQILKTSVWYQEVWNDEFLSWNSSMFDEIREISLPLSAIWAPDIIINEFVDIERSPDLPYVYV
NSSGTIENYKPIQVVSACSLETYAFPFDVQNCSLTFKSILHTVEDVDLAFLRSPEDIQHDKKAFLNDSEW
ELLSVSSTYSILQSSAGGFAQIQFNVVMRRHPLVYVVSLLIPSIFLMLVDLGSFYLPPNCRARIVFKTSVL
VGYTVFRVNMSNQVPRSVGSTPLIGHFFTICMAFLVLSLAKSIVLVKFLHDEQRGGQEQPFLCLRGDTD
ADRPRVEPRAQRAVVTESSLYGEHLAQPGTLKEVWSQLQSISNYLQTQDQTDQQEAEWLVLLSRFDR
LLFQSYLFMLGIYTITLCSLWALWGGV

Figure 1A

Nucleotide sequence of human 5-HT3B cDNA (C 452) (SEQ ID NO:1)

AGAAATTGAGCGGCATTCCATCTGGTAGGCAAGTTTGCATTTCTCCTTTTTGGGATCTGCCCAGGA
ATGTTGTCAAGTGTAATGGCTCCCCTGTGGGCCTGCATCCTGGTGGCTGCAGGAATTCTAGCCACA
GATACACATCATCCCCAGGATTCTGCTCTGTATCATCTCAGCAAGCAGCTATTACAGAAATATCAT
AAAGAAGTGAGACCTGTTTACAACTGGACCAAGGCCACCACAGTCTACCTGGACCTGTTCGTCCA
TGCTATATTGGATGTGGATGCAGAGAATCAAATATTAAAGACAAGTGTATGGTACCAAGAGGTCT
GGAATGATGAATTTTTATCCTGGAACTCCAGCATGTTTGATGAGATTAGAGAGATCTCCCTACCTC
TAAGTGCCATCTGGGCCCCCGATATCATCATCAATGAGTTTGTGGACATTGAAAGATCCCCTGACC
TTCCCTATGTTTATGTGAACTCATCTGGGACCATTGAGAACTATAAGCCCATCCAGGTGGTCTCTG
CGTGCAGTTTAGAGACATATGCTTTTCCATTTGATGTCCAGAATTGCAGCCTGACCTTCAAGAGCA
TTCTGCATACAGTGGAAGACGTAGACCTGGCCTTTCTGAGGAGCCCAGAAGACATTCAGCATGAC
AAAAAGGCGTTTTTGAATGACAGTGAGTGGGAACTTCTATCTGTGTCCTCCACATACAGCATCCTG
CAGAGCAGCGCTGGAGGATTTGCACAGATTCAGTTTAATGTGGTGATGCGCAGGCACCCCCTGGT
CTATGTCGTGAGTCTGCTGATTCCTAGCATCTTTCTCATGCTGGTGGACCTGGGGAGCTTCTACCTG
CCACCCAACTGCCGAGCCAGGATTGTGTTCAAGACCAGTGTGCTGGTGGGCTACACCGTCTTCAG
GGTCAACATGTCCAACCAGGTGCCACGGAGTGTAGGGAGCACCCCTCTGATTGGGCACTTCTTCA
CCATCTGCATGGCCTTCTTGGTTCTCAGCTTAGCTAAGTCCATCGTGTTGGTCAAATTCCTCCATGA
TGAGCAGCGTGGTGGACAGGAGCAGCCCTTCTTGTGCCTTCGAGGGGACACCGATGCTGACAGGC
CTAGAGTGGAACCCAGGGCCCAACGTGCTGTGGTAACAGAGTCCTCGCTGTATGGAGAGCACCTG
GCCCAGCCAGGAACCCTGAAGGAAGTCTGGTCGCAGCTTCAATCTATCAGCAACTACCTCCAAAC
TCAGGACCAGACAGACCAACAGGAGGCAGAGTGGCTGGTCCTCCTGTCCCGCTTTGACCGACTGC
TCTTCCAAAGCTACCTTTTCATGCTGGGGATCTACACCATCACTCTGTGCTCCCTCTGGGCACTGTG
GGGCGGCGTGTGAAGACTGAAGTGTTCTTCAGTAATTGTGCTGGCACTTAGGAGAGAGAGGAGGG
GGAATAATAGTGGGTTAAAAAGCTTTCTGGGTCGGGTGTGGTGGTTCTTGCCTATAGTCCCAGTGC
TTTGGGAGGCCATAGCAGGAGGATTGCTTGAGCCCAGGAGTTCGAGACCAGCCAGAGCAACATAG
TGAGACCACATCTCTACCAGTAAATAAATAAATAAATA

Figure 2A

Polypeptide sequence of human 5-HT3B (Tyrosine 129) (SEQ ID NO:4)

MLSSVMAPLWACILVAAGILATDTHHPQDSALYHLSKQLLQKYHKEVRPVYNWTKATTVYLDLFVH
AILDVDAENQILKTSVWYQEVWNDEFLSWNSSMFDEIREISLPLSAIWAPDIINEFVDIERYPDLPYVYV
NSSGTIENYKPIQVVSACSLETYAFPFDVQNCSLTFKSILHTVEDVDLAFLRSPEDIQHDKKAFLNDSEW
ELLSVSSTYSILQSSAGGFAQIQFNVVMRRHPLVYVVSLLIPSIFLMLVDLGSFYLPPNCRARIVFKTSVL
VGYTVFRVNMSNQVPRSVGSTPLIGHFFTICMAFLVLSLAKSIVLVKFLHDEQRGGQEQPFLCLRGDTD
ADRPRVEPRAQRAVVTESSLYGEHLAQPGTLKEVWSQLQSISNYLQTQDQTDQQEAEWLVLLSRFDR
LLFQSYLFMLGIYTITLCSLWALWGGV

Figure 1B

Nucleotide sequence of human 5-HT3B cDNA (A 452) (SEQ ID NO:3)

AGAAATTGAGCGGCATTCCATCTGGTAGGCAAGTTTGCATTTCTCCTTTTTGGGATCTGCCCAGGA
ATGTTGTCAAGTGTAATGGCTCCCCTGTGGGCCTGCATCCTGGTGGCTGCAGGAATTCTAGCCACA
GATACACATCATCCCCAGGATTCTGCTCTGTATCATCTCAGCAAGCAGCTATTACAGAAATATCAT
AAAGAAGTGAGACCTGTTTACAACTGGACCAAGGCCACCACAGTCTACCTGGACCTGTTCGTCCA
TGCTATATTGGATGTGGATGCAGAGAATCAAATATTAAAGACAAGTGTATGGTACCAAGAGGTCT
GGAATGATGAATTTTTATCCTGGAACTCCAGCATGTTTGATGAGATTAGAGAGATCTCCCTACCTC
TAAGTGCCATCTGGGCCCCCGATATCATCATCAATGAGTTTGTGGACATTGAAAGATACCCTGACC
TTCCCTATGTTTATGTGAACTCATCTGGGACCATTGAGAACTATAAGCCCATCCAGGTGGTCTCTG
CGTGCAGTTTAGAGACATATGCTTTTCCATTTGATGTCCAGAATTGCAGCCTGACCTTCAAGAGCA
TTCTGCATACAGTGGAAGACGTAGACCTGGCCTTTCTGAGGAGCCCAGAAGACATTCAGCATGAC
AAAAAGGCGTTTTTGAATGACAGTGAGTGGGAACTTCTATCTGTGTCCTCCACATACAGCATCCTG
CAGAGCAGCGCTGGAGGATTTGCACAGATTCAGTTTAATGTGGTGATGCGCAGGCACCCCCTGGT
CTATGTCGTGAGTCTGCTGATTCCTAGCATCTTTCTCATGCTGGTGGACCTGGGGAGCTTCTACCTG
CCACCCAACTGCCGAGCCAGGATTGTGTTCAAGACCAGTGTGCTGGTGGGCTACACCGTCTTCAG
GGTCAACATGTCCAACCAGGTGCCACGGAGTGTAGGGAGCACCCCTCTGATTGGGCACTTCTTCA
CCATCTGCATGGCCTTCTTGGTTCTCAGCTTAGCTAAGTCCATCGTGTTGGTCAAATTCCTCCATGA
TGAGCAGCGTGGTGGACAGGAGCAGCCCTTCTTGTGCCTTCGAGGGGACACCGATGCTGACAGGC
CTAGAGTGGAACCCAGGGCCCAACGTGCTGTGGTAACAGAGTCCTCGCTGTATGGAGAGCACCTG
GCCCAGCCAGGAACCCTGAAGGAAGTCTGGTCGCAGCTTCAATCTATCAGCAACTACCTCCAAAC
TCAGGACCAGACAGACCAACAGGAGGCAGAGTGGCTGGTCCTCCTGTCCCGCTTTGACCGACTGC
TCTTCCAAAGCTACCTTTTCATGCTGGGGATCTACACCATCACTCTGTGCTCCCTCTGGGCACTGTG
GGGCGGCGTGTGAAGACTGAAGTGTTCTTCAGTAATTGTGCTGGCACTTAGGAGAGAGAGGAGGG
GGAATAATAGTGGGTTAAAAAGCTTTCTGGGTCGGGTGTGGTGGTTCTTGCCTATAGTCCCAGTGC
TTTGGGAGGCCATAGCAGGAGGATTGCTTGAGCCCAGGAGTTCGAGACCAGCCAGAGCAACATAG
TGAGACCACATCTCTACCAGTAAATAAATAAATAAATA

Figure 2B

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1613 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 67...1389
      (D) OTHER INFORMATION:

(xi) SEQUENCE DESCRIPTION: SEQ ID NO:1:

```
AGAAATTGAG CGGCATTCCA TCTGGTAGGC AAGTTTGCAT TTCTCCTTTT TGGGATCTGC      60

CCAGGA ATG TTG TCA AGT GTA ATG GCT CCC CTG TGG GCC TGC ATC CTG        108
       Met Leu Ser Ser Val Met Ala Pro Leu Trp Ala Cys Ile Leu
        1               5                  10

GTG GCT GCA GGA ATT CTA GCC ACA GAT ACA CAT CAT CCC CAG GAT TCT       156
Val Ala Ala Gly Ile Leu Ala Thr Asp Thr His His Pro Gln Asp Ser
 15              20                  25                  30

GCT CTG TAT CAT CTC AGC AAG CAG CTA TTA CAG AAA TAT CAT AAA GAA       204
Ala Leu Tyr His Leu Ser Lys Gln Leu Leu Gln Lys Tyr His Lys Glu
                 35                  40                  45

GTG AGA CCT GTT TAC AAC TGG ACC AAG GCC ACC ACA GTC TAC CTG GAC       252
Val Arg Pro Val Tyr Asn Trp Thr Lys Ala Thr Thr Val Tyr Leu Asp
             50                  55                  60

CTG TTC GTC CAT GCT ATA TTG GAT GTG GAT GCA GAG AAT CAA ATA TTA       300
Leu Phe Val His Ala Ile Leu Asp Val Asp Ala Glu Asn Gln Ile Leu
             65                  70                  75

AAG ACA AGT GTA TGG TAC CAA GAG GTC TGG AAT GAT GAA TTT TTA TCC       348
Lys Thr Ser Val Trp Tyr Gln Glu Val Trp Asn Asp Glu Phe Leu Ser
 80                  85                  90

TGG AAC TCC AGC ATG TTT GAT GAG ATT AGA GAG ATC TCC CTA CCT CTA       396
Trp Asn Ser Ser Met Phe Asp Glu Ile Arg Glu Ile Ser Leu Pro Leu
 95                 100                 105                 110

AGT GCC ATC TGG GCC CCC GAT ATC ATC ATC AAT GAG TTT GTG GAC ATT       444
Ser Ala Ile Trp Ala Pro Asp Ile Ile Ile Asn Glu Phe Val Asp Ile
                115                 120                 125

GAA AGA TCC CCT GAC CTT CCC TAT GTT TAT GTG AAC TCA TCT GGG ACC       492
Glu Arg Ser Pro Asp Leu Pro Tyr Val Tyr Val Asn Ser Ser Gly Thr
                130                 135                 140

ATT GAG AAC TAT AAG CCC ATC CAG GTG GTC TCT GCG TGC AGT TTA GAG       540
Ile Glu Asn Tyr Lys Pro Ile Gln Val Val Ser Ala Cys Ser Leu Glu
                145                 150                 155

ACA TAT GCT TTT CCA TTT GAT GTC CAG AAT TGC AGC CTG ACC TTC AAG       588
Thr Tyr Ala Phe Pro Phe Asp Val Gln Asn Cys Ser Leu Thr Phe Lys
        160                 165                 170

AGC ATT CTG CAT ACA GTG GAA GAC GTA GAC CTG GCC TTT CTG AGG AGC       636
Ser Ile Leu His Thr Val Glu Asp Val Asp Leu Ala Phe Leu Arg Ser
175                 180                 185                 190

CCA GAA GAC ATT CAG CAT GAC AAA AAG GCG TTT TTG AAT GAC AGT GAG       684
Pro Glu Asp Ile Gln His Asp Lys Lys Ala Phe Leu Asn Asp Ser Glu
                195                 200                 205

TGG GAA CTT CTA TCT GTG TCC TCC ACA TAC AGC ATC CTG CAG AGC AGC       732
Trp Glu Leu Leu Ser Val Ser Ser Thr Tyr Ser Ile Leu Gln Ser Ser
                210                 215                 220

GCT GGA GGA TTT GCA CAG ATT CAG TTT AAT GTG GTG ATG CGC AGG CAC       780
Ala Gly Gly Phe Ala Gln Ile Gln Phe Asn Val Val Met Arg Arg His
                225                 230                 235

CCC CTG GTC TAT GTC GTG AGT CTG CTG ATT CCT AGC ATC TTT CTC ATG       828
Pro Leu Val Tyr Val Val Ser Leu Leu Ile Pro Ser Ile Phe Leu Met
        240                 245                 250

CTG GTG GAC CTG GGG AGC TTC TAC CTG CCA CCC AAC TGC CGA GCC AGG       876
Leu Val Asp Leu Gly Ser Phe Tyr Leu Pro Pro Asn Cys Arg Ala Arg
255                 260                 265                 270

ATT GTG TTC AAG ACC AGT GTG CTG GTG GGC TAC ACC GTC TTC AGG GTC       924
Ile Val Phe Lys Thr Ser Val Leu Val Gly Tyr Thr Val Phe Arg Val
                275                 280                 285

AAC ATG TCC AAC CAG GTG CCA CGG AGT GTA GGG AGC ACC CCT CTG ATT       972
Asn Met Ser Asn Gln Val Pro Arg Ser Val Gly Ser Thr Pro Leu Ile
                290                 295                 300
```

```
GGG CAC TTC TTC ACC ATC TGC ATG GCC TTC TTG GTT CTC AGC TTA GCT    1020
Gly His Phe Phe Thr Ile Cys Met Ala Phe Leu Val Leu Ser Leu Ala
        305                 310                 315

AAG TCC ATC GTG TTG GTC AAA TTC CTC CAT GAT GAG CAG CGT GGT GGA    1068
Lys Ser Ile Val Leu Val Lys Phe Leu His Asp Glu Gln Arg Gly Gly
        320                 325                 330

CAG GAG CAG CCC TTC TTG TGC CTT CGA GGG GAC ACC GAT GCT GAC AGG    1116
Gln Glu Gln Pro Phe Leu Cys Leu Arg Gly Asp Thr Asp Ala Asp Arg
335                 340                 345                 350

CCT AGA GTG GAA CCC AGG GCC CAA CGT GCT GTG GTA ACA GAG TCC TCG    1164
Pro Arg Val Glu Pro Arg Ala Gln Arg Ala Val Val Thr Glu Ser Ser
            355                 360                 365

CTG TAT GGA GAG CAC CTG GCC CAG CCA GGA ACC CTG AAG GAA GTC TGG    1212
Leu Tyr Gly Glu His Leu Ala Gln Pro Gly Thr Leu Lys Glu Val Trp
        370                 375                 380

TCG CAG CTT CAA TCT ATC AGC AAC TAC CTC CAA ACT CAG GAC CAG ACA    1260
Ser Gln Leu Gln Ser Ile Ser Asn Tyr Leu Gln Thr Gln Asp Gln Thr
        385                 390                 395

GAC CAA CAG GAG GCA GAG TGG CTG GTC CTC CTG TCC CGC TTT GAC CGA    1308
Asp Gln Gln Glu Ala Glu Trp Leu Val Leu Leu Ser Arg Phe Asp Arg
        400                 405                 410

CTG CTC TTC CAA AGC TAC CTT TTC ATG CTG GGG ATC TAC ACC ATC ACT    1356
Leu Leu Phe Gln Ser Tyr Leu Phe Met Leu Gly Ile Tyr Thr Ile Thr
415                 420                 425                 430

CTG TGC TCC CTC TGG GCA CTG TGG GGC GGC GTG TGAAGACTGA AGTGTTCTTC  1409
Leu Cys Ser Leu Trp Ala Leu Trp Gly Gly Val
                435                 440

AGTAATTGTG CTGGCACTTA GGAGAGAGAG GAGGGGGAAT AATAGTGGGT TAAAAAGCTT  1469

TCTGGGTCGG GTGTGGTGGT TCTTGCCTAT AGTCCCAGTG CTTTGGGAGG CCATAGCAGG  1529

AGGATTGCTT GAGCCCAGGA GTTCGAGACC AGCCAGAGCA ACATAGTGAG ACCACATCTC  1589

TACCAGTAAA TAAATAAATA AATA                                         1613

(2) INFORMATION FOR SEQ ID NO:2:

(i) SEQUENCE CHARACTERISTICS:
        (A) LENGTH: 441 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Leu Ser Ser Val Met Ala Pro Leu Trp Ala Cys Ile Leu Val Ala
1               5                   10                  15

Ala Gly Ile Leu Ala Thr Asp Thr His His Pro Gln Asp Ser Ala Leu
            20                  25                  30

Tyr His Leu Ser Lys Gln Leu Leu Gln Lys Tyr His Lys Glu Val Arg
        35                  40                  45

Pro Val Tyr Asn Trp Thr Lys Ala Thr Thr Val Tyr Leu Asp Leu Phe
    50                  55                  60

Val His Ala Ile Leu Asp Val Asp Ala Glu Asn Gln Ile Leu Lys Thr
65                  70                  75                  80

Ser Val Trp Tyr Gln Glu Val Trp Asn Asp Glu Phe Leu Ser Trp Asn
                85                  90                  95

Ser Ser Met Phe Asp Glu Ile Arg Glu Ile Ser Leu Pro Leu Ser Ala
```

-continued

```
                100                 105                 110
Ile Trp Ala Pro Asp Ile Ile Asn Glu Phe Val Asp Ile Glu Arg
        115                 120                 125
Ser Pro Asp Leu Pro Tyr Val Tyr Val Asn Ser Ser Gly Thr Ile Glu
    130                 135                 140
Asn Tyr Lys Pro Ile Gln Val Val Ser Ala Cys Ser Leu Glu Thr Tyr
145                 150                 155                 160
Ala Phe Pro Phe Asp Val Gln Asn Cys Ser Leu Thr Phe Lys Ser Ile
                165                 170                 175
Leu His Thr Val Glu Asp Val Asp Leu Ala Phe Leu Arg Ser Pro Glu
            180                 185                 190
Asp Ile Gln His Asp Lys Lys Ala Phe Leu Asn Asp Ser Glu Trp Glu
        195                 200                 205
Leu Leu Ser Val Ser Ser Thr Tyr Ser Ile Leu Gln Ser Ser Ala Gly
    210                 215                 220
Gly Phe Ala Gln Ile Gln Phe Asn Val Val Met Arg Arg His Pro Leu
225                 230                 235                 240
Val Tyr Val Val Ser Leu Leu Ile Pro Ser Ile Phe Leu Met Leu Val
                245                 250                 255
Asp Leu Gly Ser Phe Tyr Leu Pro Pro Asn Cys Arg Ala Arg Ile Val
            260                 265                 270
Phe Lys Thr Ser Val Leu Val Gly Tyr Thr Val Phe Arg Val Asn Met
        275                 280                 285
Ser Asn Gln Val Pro Arg Ser Val Gly Ser Thr Pro Leu Ile Gly His
    290                 295                 300
Phe Phe Thr Ile Cys Met Ala Phe Leu Val Leu Ser Leu Ala Lys Ser
305                 310                 315                 320
Ile Val Leu Val Lys Phe Leu His Asp Glu Gln Arg Gly Gly Gln Glu
                325                 330                 335
Gln Pro Phe Leu Cys Leu Arg Gly Asp Thr Asp Ala Asp Arg Pro Arg
            340                 345                 350
Val Glu Pro Arg Ala Gln Arg Ala Val Val Thr Glu Ser Ser Leu Tyr
        355                 360                 365
Gly Glu His Leu Ala Gln Pro Gly Thr Leu Lys Glu Val Trp Ser Gln
    370                 375                 380
Leu Gln Ser Ile Ser Asn Tyr Leu Gln Thr Gln Asp Gln Thr Asp Gln
385                 390                 395                 400
Gln Glu Ala Glu Trp Leu Val Leu Leu Ser Arg Phe Asp Arg Leu Leu
                405                 410                 415
Phe Gln Ser Tyr Leu Phe Met Leu Gly Ile Tyr Thr Ile Thr Leu Cys
            420                 425                 430
Ser Leu Trp Ala Leu Trp Gly Gly Val
        435                 440
```

(2) INFORMATION FOR SEQ ID NO:3:

(i) SEQUENCE CHARACTERISTICS:
        (A) LENGTH: 1613 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 67...1389
        (D) OTHER INFORMATION:

(xi) SEQUENCE DESCRIPTION: SEQ ID NO:3:

```
AGAAATTGAG CGGCATTCCA TCTGGTAGGC AAGTTTGCAT TTCTCCTTTT TGGGATCTGC      60

CCAGGA ATG TTG TCA AGT GTA ATG GCT CCC CTG TGG GCC TGC ATC CTG        108
       Met Leu Ser Ser Val Met Ala Pro Leu Trp Ala Cys Ile Leu
         1               5                  10

GTG GCT GCA GGA ATT CTA GCC ACA GAT ACA CAT CAT CCC CAG GAT TCT       156
Val Ala Ala Gly Ile Leu Ala Thr Asp Thr His His Pro Gln Asp Ser
 15              20                  25                  30

GCT CTG TAT CAT CTC AGC AAG CAG CTA TTA CAG AAA TAT CAT AAA GAA       204
Ala Leu Tyr His Leu Ser Lys Gln Leu Leu Gln Lys Tyr His Lys Glu
                 35                  40                  45

GTG AGA CCT GTT TAC AAC TGG ACC AAG GCC ACC ACA GTC TAC CTG GAC       252
Val Arg Pro Val Tyr Asn Trp Thr Lys Ala Thr Thr Val Tyr Leu Asp
             50                  55                  60

CTG TTC GTC CAT GCT ATA TTG GAT GTG GAT GCA GAG AAT CAA ATA TTA       300
Leu Phe Val His Ala Ile Leu Asp Val Asp Ala Glu Asn Gln Ile Leu
         65                  70                  75

AAG ACA AGT GTA TGG TAC CAA GAG GTC TGG AAT GAT GAA TTT TTA TCC       348
Lys Thr Ser Val Trp Tyr Gln Glu Val Trp Asn Asp Glu Phe Leu Ser
     80                  85                  90

TGG AAC TCC AGC ATG TTT GAT GAG ATT AGA GAG ATC TCC CTA CCT CTA       396
Trp Asn Ser Ser Met Phe Asp Glu Ile Arg Glu Ile Ser Leu Pro Leu
 95                 100                 105                 110

AGT GCC ATC TGG GCC CCC GAT ATC ATC ATC AAT GAG TTT GTG GAC ATT       444
Ser Ala Ile Trp Ala Pro Asp Ile Ile Ile Asn Glu Phe Val Asp Ile
                115                 120                 125

GAA AGA TAC CCT GAC CTT CCC TAT GTT TAT GTG AAC TCA TCT GGG ACC       492
Glu Arg Tyr Pro Asp Leu Pro Tyr Val Tyr Val Asn Ser Ser Gly Thr
            130                 135                 140

ATT GAG AAC TAT AAG CCC ATC CAG GTG GTC TCT GCG TGC AGT TTA GAG       540
Ile Glu Asn Tyr Lys Pro Ile Gln Val Val Ser Ala Cys Ser Leu Glu
        145                 150                 155

ACA TAT GCT TTT CCA TTT GAT GTC CAG AAT TGC AGC CTG ACC TTC AAG       588
Thr Tyr Ala Phe Pro Phe Asp Val Gln Asn Cys Ser Leu Thr Phe Lys
    160                 165                 170

AGC ATT CTG CAT ACA GTG GAA GAC GTA GAC CTG GCC TTT CTG AGG AGC       636
Ser Ile Leu His Thr Val Glu Asp Val Asp Leu Ala Phe Leu Arg Ser
175                 180                 185                 190

CCA GAA GAC ATT CAG CAT GAC AAA AAG GCG TTT TTG AAT GAC AGT GAG       684
Pro Glu Asp Ile Gln His Asp Lys Lys Ala Phe Leu Asn Asp Ser Glu
                195                 200                 205

TGG GAA CTT CTA TCT GTG TCC TCC ACA TAC AGC ATC CTG CAG AGC AGC       732
Trp Glu Leu Leu Ser Val Ser Ser Thr Tyr Ser Ile Leu Gln Ser Ser
            210                 215                 220

GCT GGA GGA TTT GCA CAG ATT CAG TTT AAT GTG GTG ATG CGC AGG CAC       780
Ala Gly Gly Phe Ala Gln Ile Gln Phe Asn Val Val Met Arg Arg His
        225                 230                 235

CCC CTG GTC TAT GTC GTG AGT CTG CTG ATT CCT AGC ATC TTT CTC ATG       828
Pro Leu Val Tyr Val Val Ser Leu Leu Ile Pro Ser Ile Phe Leu Met
    240                 245                 250

CTG GTG GAC CTG GGG AGC TTC TAC CTG CCA CCC AAC TGC CGA GCC AGG       876
Leu Val Asp Leu Gly Ser Phe Tyr Leu Pro Pro Asn Cys Arg Ala Arg
255                 260                 265                 270

ATT GTG TTC AAG ACC AGT GTG CTG GTG GGC TAC ACC GTC TTC AGG GTC       924
Ile Val Phe Lys Thr Ser Val Leu Val Gly Tyr Thr Val Phe Arg Val
                275                 280                 285

AAC ATG TCC AAC CAG GTG CCA CGG AGT GTA GGG AGC ACC CCT CTG ATT       972
Asn Met Ser Asn Gln Val Pro Arg Ser Val Gly Ser Thr Pro Leu Ile
            290                 295                 300
```

```
GGG CAC TTC TTC ACC ATC TGC ATG GCC TTC TTG GTT CTC AGC TTA GCT    1020
Gly His Phe Phe Thr Ile Cys Met Ala Phe Leu Val Leu Ser Leu Ala
            305                 310                 315

AAG TCC ATC GTG TTG GTC AAA TTC CTC CAT GAT GAG CAG CGT GGT GGA    1068
Lys Ser Ile Val Leu Val Lys Phe Leu His Asp Glu Gln Arg Gly Gly
        320                 325                 330

CAG GAG CAG CCC TTC TTG TGC CTT CGA GGG GAC ACC GAT GCT GAC AGG    1116
Gln Glu Gln Pro Phe Leu Cys Leu Arg Gly Asp Thr Asp Ala Asp Arg
335                 340                 345                 350

CCT AGA GTG GAA CCC AGG GCC CAA CGT GCT GTG GTA ACA GAG TCC TCG    1164
Pro Arg Val Glu Pro Arg Ala Gln Arg Ala Val Val Thr Glu Ser Ser
                355                 360                 365

CTG TAT GGA GAG CAC CTG GCC CAG CCA GGA ACC CTG AAG GAA GTC TGG    1212
Leu Tyr Gly Glu His Leu Ala Gln Pro Gly Thr Leu Lys Glu Val Trp
            370                 375                 380

TCG CAG CTT CAA TCT ATC AGC AAC TAC CTC CAA ACT CAG GAC CAG ACA    1260
Ser Gln Leu Gln Ser Ile Ser Asn Tyr Leu Gln Thr Gln Asp Gln Thr
        385                 390                 395

GAC CAA CAG GAG GCA GAG TGG CTG GTC CTC CTG TCC CGC TTT GAC CGA    1308
Asp Gln Gln Glu Ala Glu Trp Leu Val Leu Leu Ser Arg Phe Asp Arg
400                 405                 410

CTG CTC TTC CAA AGC TAC CTT TTC ATG CTG GGG ATC TAC ACC ATC ACT    1356
Leu Leu Phe Gln Ser Tyr Leu Phe Met Leu Gly Ile Tyr Thr Ile Thr
415                 420                 425                 430

CTG TGC TCC CTC TGG GCA CTG TGG GGC GGC GTG TGAAGACTGA AGTGTTCTTC  1409
Leu Cys Ser Leu Trp Ala Leu Trp Gly Gly Val
            435                 440

AGTAATTGTG CTGGCACTTA GGAGAGAGAG GAGGGGGAAT AATAGTGGGT TAAAAAGCTT  1469

TCTGGGTCGG GTGTGGTGGT TCTTGCCTAT AGTCCCAGTG CTTTGGGAGG CCATAGCAGG  1529

AGGATTGCTT GAGCCCAGGA GTTCGAGACC AGCCAGAGCA ACATAGTGAG ACCACATCTC  1589

TACCAGTAAA TAAATAAATA AATA                                        1613

(2) INFORMATION FOR SEQ ID NO:4:

(i) SEQUENCE CHARACTERISTICS:
        (A) LENGTH: 441 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

Met Leu Ser Ser Val Met Ala Pro Leu Trp Ala Cys Ile Leu Val Ala
1               5                   10                  15

Ala Gly Ile Leu Ala Thr Asp Thr His His Pro Gln Asp Ser Ala Leu
            20                  25                  30

Tyr His Leu Ser Lys Gln Leu Leu Gln Lys Tyr His Lys Glu Val Arg
        35                  40                  45

Pro Val Tyr Asn Trp Thr Lys Ala Thr Thr Val Tyr Leu Asp Leu Phe
    50                  55                  60

Val His Ala Ile Leu Asp Val Asp Ala Glu Asn Gln Ile Leu Lys Thr
65                  70                  75                  80

Ser Val Trp Tyr Gln Glu Val Trp Asn Asp Glu Phe Leu Ser Trp Asn
            85                  90                  95

Ser Ser Met Phe Asp Glu Ile Arg Glu Ile Ser Leu Pro Leu Ser Ala
```

```
              100                 105                 110
Ile Trp Ala Pro Asp Ile Ile Ile Asn Glu Phe Val Asp Ile Glu Arg
            115                 120                 125

Tyr Pro Asp Leu Pro Tyr Val Tyr Val Asn Ser Ser Gly Thr Ile Glu
130                 135                 140

Asn Tyr Lys Pro Ile Gln Val Val Ser Ala Cys Ser Leu Glu Thr Tyr
145                 150                 155                 160

Ala Phe Pro Phe Asp Val Gln Asn Cys Ser Leu Thr Phe Lys Ser Ile
                165                 170                 175

Leu His Thr Val Glu Asp Val Asp Leu Ala Phe Leu Arg Ser Pro Glu
                180                 185                 190

Asp Ile Gln His Asp Lys Lys Ala Phe Leu Asn Asp Ser Glu Trp Glu
                195                 200                 205

Leu Leu Ser Val Ser Ser Thr Tyr Ser Ile Leu Gln Ser Ser Ala Gly
            210                 215                 220

Gly Phe Ala Gln Ile Gln Phe Asn Val Val Met Arg Arg His Pro Leu
225                 230                 235                 240

Val Tyr Val Val Ser Leu Leu Ile Pro Ser Ile Phe Leu Met Leu Val
                245                 250                 255

Asp Leu Gly Ser Phe Tyr Leu Pro Pro Asn Cys Arg Ala Arg Ile Val
                260                 265                 270

Phe Lys Thr Ser Val Leu Val Gly Tyr Thr Val Phe Arg Val Asn Met
                275                 280                 285

Ser Asn Gln Val Pro Arg Ser Val Gly Ser Thr Pro Leu Ile Gly His
            290                 295                 300

Phe Phe Thr Ile Cys Met Ala Phe Leu Val Leu Ser Leu Ala Lys Ser
305                 310                 315                 320

Ile Val Leu Val Lys Phe Leu His Asp Glu Gln Arg Gly Gly Gln Glu
                325                 330                 335

Gln Pro Phe Leu Cys Leu Arg Gly Asp Thr Asp Ala Asp Arg Pro Arg
                340                 345                 350

Val Glu Pro Arg Ala Gln Arg Ala Val Val Thr Glu Ser Ser Leu Tyr
            355                 360                 365

Gly Glu His Leu Ala Gln Pro Gly Thr Leu Lys Glu Val Trp Ser Gln
            370                 375                 380

Leu Gln Ser Ile Ser Asn Tyr Leu Gln Thr Gln Asp Gln Thr Asp Gln
385                 390                 395                 400

Gln Glu Ala Glu Trp Leu Val Leu Leu Ser Arg Phe Asp Arg Leu Leu
                405                 410                 415

Phe Gln Ser Tyr Leu Phe Met Leu Gly Ile Tyr Thr Ile Thr Leu Cys
                420                 425                 430

Ser Leu Trp Ala Leu Trp Gly Gly Val
            435                 440
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

CTGGAACTCC AGCATGTTTG ATGA                      24

```
(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

TGAAGGTCAG GCTGCAATTC TGGA                                              24

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:7:

GGCCGGAAGC TTGATCTGCC CAGGAATGTT GTCAAG                                 36

(2) INFORMATION FOR SEQ ID NO:8:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:8:

CCGGCCCTCG AGCTGCAGTC TAGATACCAC GCCGCCCCAC AGTGCCCAG                   49
```

HUMAN 5-HT3 RECEPTOR

ACKNOWLEDGEMENT OF GOVERNMENT SUPPORT

This invention was made with U.S. government support under Grant Number 5R29 NS 34702-02 awarded by the Department of Health and Human Services, National Institutes of Health, National Institute of Neurological Disorders and Stroke. The U.S. government has certain rights in the invention.

TECHNICAL FIELD

The invention relates to synaptic receptors that mediate transmission in the peripheral and central nervous systems. In particular, the invention concerns a new human 5-HT3 receptor that expands the repertoire of targets for pharmaceutical compounds.

BACKGROUND ART

Synaptic transmission in the peripheral and central nervous systems is regulated by a multiplicity of ligand-gated ion channels. This superfamily of receptors includes the γ-amino butyric acid (GABA) receptor, the glycine receptor, and the acetyl choline receptor, as well as receptors responsive to serotonin (5-HT). The GABA-, glycine-, and acetylcholine-gated receptors are formed from mixtures of homologous subunits in various combinations. Serotonin-gated receptors fall into at least three subclasses. 5-HT1 and 5-HT2 receptors are described in U.S. Pat. No. 5,155,218. The 5-HT1 and 5-HT2 receptors are characterized by seven transmembrane regions; however, the 5-HT3 receptors are ligand-gated ion channels which are related structurally to the GABA, glycine and nicotinic acetylcholine receptors. A number of subtypes of 5-HT1 and 5-HT2 receptors have been found, but only a single 5-HT3 receptor unit has so far been detected in mouse, human and guinea pig tissues (Miriq et al. *Science* (1991) 254:432–437; Belelli et al. *Mol Pharmacol* (1995) 48:1054–1062; Lankiewicz et al. *Mol Pharmacol* (1997) 53:202–212). This subunit, designated herein 5-HT3A, has been 25 expressed in oocytes and HEK-293 cells and the recombinantly produced form can mimic many of the properties of the 5-HT3 receptors as they occur in tissues. However, there are sufficient differences that it is suspected that additional 5-HT3 subtypes exist (Bonhaus et al. *J Neurochem* (1993) 62:1927–1932; Van Hooft et al. *J Neurochem* (1997) 69:1318–1321; Hussy et al. *J Physiol* (1994) 418:311–323).

The existence of a multiplicity of subtypes of such receptors is important. Agonists and antagonists can be found that are selective for one subtype or another, thus resulting in different physiological consequences and expanding the repertoire of pharmaceutical substances available for therapy. This enables a more nuanced treatment of various conditions affected by receptor stimulation.

The class of serotonin receptors with which the present invention is concerned, the 5-HT3 class, is evidently involved in the induction of nausea and in behavioral disorders. Apud, *Neuropsychopharmacol* (1993) 8:117–130. Thus, antagonists of the 5-HT3 receptor would be useful in ameliorating the side-effects of many cancer therapeutic drugs (Gralla et al. *New England J Med* (1991) 305:905–909). Antagonists to this receptor would also be useful in controlling behavioral disorders (Rodgers et al. *Psychopharmacol* (1995) 117:306–312; Costall et al. *Brit J Pharmacol* (1993) 90:89; Zoldan etal. *Lancet* (1993) 341:562–563).

The present invention provides an additional subtype of the 5-HT3 subclass which thus provides an additional tool for evaluating the selectivity of candidate antagonists and agonists of the serotonin receptor class as well as providing a useful reagent for screening libraries of compounds for desired physiological activities described above.

DISCLOSURE OF THE INVENTION

The invention provides recombinant materials for the production of a previously undescribed subtype of serotonin receptor, designated herein 5-HT3B. The availability of these recombinant materials makes possible high throughput screening of candidate antiemetics and antipsychotic compounds as well as providing a tool for enhancing the selectivity of such compounds in particular individuals and in response to specific conditions.

Thus, in one aspect, the invention is directed to recombinant materials for production of 5-HT3B receptor protein. Two polymorphic forms of the protein have been found associated with a single nucleotide change in the encoding sequence. The amino acid sequences of these forms and set forth in FIGS. 1A and 1B. Also useful are sufficient contiguous fragments of these proteins so as to have substantial functional identity with that of the amino acid sequences of FIG. 1A or 1B when displayed on a cell surface, or proteins with amino acid sequences sufficiently homologous to display the same functional characteristics.

In other aspects, the invention is directed to cells displaying the proteins of FIG. 1A or 1B in a functionally active form and to methods to identify agonists and antagonists of the associated receptor function in assay systems using such cells. The agonists and antagonists identified according to this screen are useful in treating nausea and psychological disorders. The invention is also directed to antibodies that recognize the 5-HT3B receptors, which are useful in purification of this protein, and to oligonucleotide constructs that modulate the production of the receptor in tissues.

BRIEF DESCRIPTION OF THE DRAWINGS

FIG. 1A (SEQ. ID No:2) shows the amino acid sequence of the human $Ser^{129}$ 5-HT3B receptor.

FIG. 1B (SEQ. ID No:4) shows the amino acid sequence of the human $Tyr^{129}$ 5-HT3B receptor.

FIGS. 2A (SEQ. ID No:1) and 2B (SEQ. ID No:3) show the nucleotide sequences of cDNAs encoding the amino acid sequences of FIGS. 1A and 1B.

MODES OF CARRYING OUT THE INVENTION

The amino acid sequences set forth in FIGS. 1A and 1B herein characterize a newly discovered human 5-HT3 receptor subunit, the existence of which was previously unknown. The availability of this receptor provides an additional tool for development of pharmaceuticals that are useful in controlling nausea, controlling anxiety, and in regulating other behavior disorders. This receptor contains 441 amino acid residues which display 41% amino acid identity with the human 5-HT3A subunit using the algorithm embodied in the GeneWorks 2.4 software package (Intelligenetics) to determine identity. This level of identity is similar to that found among different subunit classes of other receptor families such as the a and P classes of the GABA-, glycine-, and acetyl choline-gated channels.

It is recognized that minor changes in amino acid sequence of receptor proteins may not alter their specificity for activating ligands or their downstream signaling sequelae. Thus, included within the invention are proteins (and recombinant materials for their preparation) which proteins exhibit sufficient homology to the amino acid sequences shown for the 5-HT3B receptor in FIGS. 1A and 1B to behave in substantially the same manner. Typically, such protein sequences will exhibit 90% amino acid identity, preferably 95% amino acid identity, more preferably 98% amino acid identity and most preferably 99% amino acid identity with the referent sequence. In addition, minor portions of the sequence may be deleted without appreciably affecting the biological function of the protein and the proteins and recombinant materials of the invention include fragments containing a sufficient portion of the amino acid sequence depicted so as to exhibit the same biological function.

In addition, particular fragments of the receptor or of the nucleotide sequence encoding it are useful per se. For example, the extracellular portion of the receptor contains epitopes useful in generating an immune response as described below for the production of antibodies. In addition, such fragments may be formulated so as to elicit a cellular immune response directed against cells displaying the receptors for treatment of conditions where overproduction of the receptor is undesirably affecting the physical or psychological condition of the subject. Formulations which are designed to target the cellular immune response are generally known in the art.

In addition, fragments of the nucleotide sequence set forth in FIGS. 2A and 2B are useful as probes for detecting the presence of the gene or detecting the expression of the gene encoding the 5-HT3B receptor by measuring the mRNA levels in cells or tissues.

The invention relates to recombinant materials that can be used to produce the 5-HT3B receptor in suitable host cells which can be cultured for suitable assays. The nucleotide sequences encoding the receptor shown in FIGS. 2A and 2B represent the naturally occurring cDNA. The recombinant materials of the invention, however, include the degenerate forms of the sequences shown in FIGS. 2A and 2B, as well as nucleotide sequences that hybridize under stringent conditions with either the nucleotide sequences shown in FIGS. 2A or 2B or with their degenerate forms, thus representing sequences that encode homologous proteins. By "stringent conditions" is meant that hybridization will occur only if the nucleotide sequence to be hybridized is 90% homologous, preferably 95% homologous, more preferably 98% homologous, and most preferably 99% homologous to those shown in FIGS. 2A or 2B or their degenerate forms.

As is understood in the art, the relevant nucleotide sequences encoding the 5-HT3B receptor protein may be retrieved using the methods described herein, or other methods known in the art using the sequence information provided, or may be synthesized using commercially available instrumentation, or may be prepared using a combination of these techniques. Once obtained, the encoding nucleotide sequence will be manipulated so as to effect its expression in desired recombinant host cells. While the receptor of the invention can be produced in prokaryotic cells, other microbes, such as yeast or even in plant cells or their protoplasts, it is most useful when produced in higher eukaryotic cells such as insect cells, for example Drosophila or Sf9 cells, or animal cells, for example CHO cells, COS cells, oocytes, or HEK-293 cells. HEK-293 cells are preferred. For expression in oocytes, the nucleotide sequence may be supplied in the form of cRNA.

Suitable control sequences for expression in each desired host are by now well known in the art and expression systems for a multiplicity of appropriate hosts are available commercially. Methods for introducing the nucleotide sequence encoding the 5-HT3B receptor into host cells of various descriptions are also well known in the art. Typically, the encoding nucleotide sequence is expressed from an extrachromosomal vector such as a plasmid. However, if desired, an entire expression system may be introduced into the host cell chromosome or the nucleotide sequence may be placed under control of expression control sequences already present in the chromosome, for example by homologous recombination.

The mature 5-HT3B protein can be produced intracellularly, displayed on the surface of cells, or secreted into the medium. If the protein itself is desired, independent of the cells, it can be prepared as a mature protein or as a fusion protein. Fusion proteins may include additional elements useful in purification or labeling. For example, a series of histidine residues has been used as a convenient moiety to assist in purification of the attached protein. Such fusion elements may also provide convenient means for other manipulations of the peptide, such as coupling to label.

Alternatively, the 5-HT3B receptor can be displayed on the cell surface. The amino acid sequences set forth in FIGS. 1A and 1B herein represent the entire 5-HT3B subunit including its signal sequence. For display of the receptor at the cell surface, an alternative signal sequence may be substituted. Thus a heterologous signal sequence may be ligated to the 5' end of the nucleotide sequence encoding the protein which provides the functional 5-HT3B receptor. Preferably, the signal sequence associated with the 5-HT3A subunit may be employed, and ligated to the 5-HT3B encoding sequence upstream of the codon for amino acid 16–26, preferably 18–20.

Cells expressing the receptor protein of the invention are useful in screening compounds that are agonists or antagonists of the receptor.

To screen for agonist activity, cells displaying the receptor are contacted with a compound to be tested and the presence or absence or amount of the functional response to activation of the receptor is observed. For example, the electrical properties of transfected cells, such as HEK-293 cells, are recorded in the whole cell voltage clamp configuration as described by Hamil et al. *Pflueg Arch Eur J Physiol* (1981) 391:85–100, under visual control using an inverted microscope as described by Lankiewicz et al. *Mol Pharmacol* (1997) 53:202–212. To screen for antagonists, cells displaying the receptor are incubated in the presence of both a known agonist, such as serotonin, and the candidate compound. The effect of the candidate compound on the functional response to the agonist is then observed. Compounds that diminish the functional response are identified as antagonists.

Antagonists can also be identified simply by their ability to bind the receptor, either testing such binding directly, or, more commonly, in competition with a labeled known agonist or antagonist. Of course, a variety of labels can be used in either format, including enzyme, fluorescent, and radioisotope labels. A multiplicity of assay formats to assess the binding of a candidate compound to a target protein is known. In one commonly used assay, membranes prepared from transfected HEK-293 cells are incubated with tritiated GR65630 and bound ligand is separated from free ligand by filtration as described by Lankiewicz et al. *Mol Pharmacol* (1997) supra. Antagonists to the receptor will be useful as pharmaceuticals in treating the nausea associated with chemotherapy, in treating high levels of anxiety, and in other psychological disorders such as aversion, psychotic disorders, depression, cognition disorders, and drug addiction. A review of conditions that involve 5-HT3 receptors is provided by Greenshaw *Trends Pharmacol Sci* (1993) 14:265–270.

Under certain circumstances, pharmaceutical compositions containing agonists will also be beneficial as analgesics as described by Alhaider et al. *J Neurosci* (1991) 11:1881–1888.

In addition to, for example, small molecule antagonists identified by the assays set forth above, alternative mechanisms to antagonize the receptor response may also be employed. Antibodies which are immunoreactive with the extracellular portions of the receptor are useful in this regard. Antibodies may be prepared, for example using the epitopes that are external to the cell surface, which can be identified using art-known methods, in generally understood techniques by eliciting an immune response in a suitable vertebrate subject such as a rabbit, rat or mouse. It may be necessary to couple the desired epitopes to an immunogenic carrier such as KLH or diphtheria toxoid in order to enhance the immune response, or the epitopes may be included in a larger protein, including the native 5-HT3B subunit itself Epitopes may also be present in tandem in a single amino acid sequence in order to enhance immunogenicity.

The polyclonal antisera directly obtained from immunization are useful, for example, in purifying the 5-HT3B receptor protein and in assaying samples for the presence of this receptor. Antibodies also include antiidiotypes. Antibodies which have undesirable cross-reactivities can be identified and removed from antisera using suitable affinity chromatographic techniques. For use as a pharmaceutical in antagonizing the receptor in situ, monoclonal antibodies are preferred. (Of course, monoclonal antibodies can be used for purification and assay as well.) Techniques for preparing monoclonal antibodies are well known and suitable immortalized cells producing antibodies of the correct specificity can be assessed by using the recombinant cells displaying the receptor, for example, or using the immunizing epitopes as antigens in suitable assays such as ELISA or RIA. By suitable design of screening assays, monoclonal antibodies which are specific for the 5-HT3B receptor and thus do not significantly cross-react with other, perhaps similar proteins, can be identified.

Antibodies may also conveniently be produced recombinantly by retrieving the genes encoding the monoclonal antibodies described above. Recombinant expression permits the production of single-chain antibodies as well as chimeric and humanized forms of antibodies specific to the 5-HT3B receptor protein. These antibodies may be used as antagonists in the manner set forth above.

As is understood in the art, the variable region of antibodies is responsible for their binding affinity, and thus, fragments of whole antibodies may be used, such as the Fab fragment, the Fab' fragment, or the F(ab')$_2$ fragment; these fragments can be prepared by proteolytic cleavage of whole antibodies or may be produced recombinantly. Recombinant production also permits production of the single-chain F$_v$ form.

Fragments of antibodies are particularly useful in context where only binding to target is required. Thus, in addition to use in therapeutic compositions where their activity as antagonists is exploited, the antibodies or fragments may be labeled and used as a diagnostic tool to locate high concentrations of serotonin receptors in various tissues. Accordingly, individuals with higher or lower expression levels than those exhibited by normal control subjects can be identified. Individuals with high levels of expression as compared to control normal subjects are characterized by disorders such as high levels of anxiety, and other psychotic disorders such as a propensity for drug addiction. Persons with low levels of expression may exhibit other psychological disorders. Suitably radio-labeled antibody fragments may be used to measure these levels of expression, for example, in the brain.

Alternatively, the activity of the 5-HT3B receptor can be modulated by controlling its production and display in a subject. Various techniques for inhibiting transcription or translation of a nucleotide sequence are known. Such control may be effected through antisense constructs utilizing the information provided by the nucleotide sequences set forth in FIGS. 2A and 2B. Antisense oligonucleotides can be supplied directly or expression systems for generating such antisense sequences may be employed. Further, transcription may be interrupted by utilizing nucleotide sequences that form a triple helix with the double-stranded gene. Sequence-specific oligonucleotides designed to form triple helices have been described by Dervan et al. *Science* (1991) 251:1360–1365 and by Cooney et al. *Science* (1988) 241:456–460.

The progress of the effect of the treatment described above to modulate the production of 5-HT3B receptors may, if desired, be monitored using the labeled antibodies as a diagnostic tool as described above.

The availability of the nucleotide sequence encoding the 5-HT3B receptor also provides a material useful in gene therapy to correct conditions characterized by an inadequate production of this receptor.

Thus, the invention provides a newly discovered serotonin receptor that is significant in regulating the flow of signals through the nervous system and which represents a target for pharmaceuticals for modulation of this system and its metabolic consequences.

The availability of the nucleotide sequence encoding the 5-HT3B receptor provides a control against which mutations in the gene can be measured in various subjects. Thus, having available the sequence of the control "normal" gene permits detection and identification of mutations. Tracking the occurrence of such mutations and correlating them with the incidence of disorders related to defective or inadequately produced 5-HT3B receptors provides a basis for genetic diagnosis of individuals with a propensity for such disorders.

The following examples are intended to illustrate but not to limit the invention.

EXAMPLE 1

Isolation of Human 5-HT3B

A cDNA library from human fetal brain was amplified by anchored PCR methodology as described by Hanna et al. *Genomics* (1997) 43:384–386. The oligonucleotide primers were:

(1) 5'-CTGGAACTCCAGCATGTTTGATGA (SEQ. ID No:5)

(2) 5'-TGAAGGTCAGGCTGCAATTCTGGA (SEQ. ID No:6)

These primers were selected based on nucleotide sequences contained in GenBank Accession No. AC002290 which consists of 20 unordered nucleotide fragments from a PAC clone (pDJ105h16) that was derived from human chromosome 11 q23.1. This clone is not annotated, but was identified as encoding a serotonin receptor by the observation that it includes three nucleotide fragments that encode peptides of 38, 56 and 71 residues, each of which displays 50–60% similarity to regions of a query sequence representing the human 5-HT3A subunit (Belelli et al. *Mol Pharmacol* (1995) 48:1054–1062).

The amplification protocol was at 95° C. for 45 sec., 60° C. for 60 sec., 72° C. for two min. for 40 cycles using the XL-PCR system (Perkin Elmer).

A number of cDNA fragments were obtained and the terminal sequences were used to design primers 3 and 4 for amplification of the entire sequence of the 5-HT3B subunit.

(3) 5'-ggccggaagcttGATCTGCCCAGGAATGTT GTCAAG (SEQ. ID No:7)

(4) 5'-ccggccctcgagctgcagtctagaTACCACGCCG CCCCACAGTGCCCAG (SEQ. ID No:8)

The resulting cDNA was sequenced, and the open reading frame which encodes the 5-HT3B subunit was cloned into pCDM8 (Invitrogen).

The sequence of the open reading frame for two polymorphic forms of human 5-HT3B is shown in FIGS. 2A and 2B and the deduced amino acid sequences are shown in FIGS. 1A and 1B. The subunit contains 441 amino acid residues with 41% amino acid identity with human 5-HT3A extending over the entire length of the mature subunits. The only difference between the two forms is in the identity of the nucleotide at position 452 which is C. in FIG. 2A and A in FIG. 2B. This results in a change in the encoded amino acid so that the protein of FIG. 1A contains a serine residue at position 129 and that in FIG. 1B contains a tyrosine at that position.

EXAMPLE 2

Determination of 5-HT3B Expression in Tissues

Using nucleotides 936–1392 as a probe, Northern analysis of human mRNA samples derived from various tissues shows expression of 5-HT3B in brain, testes and kidney. No mRNA transcript was detectable in samples of heart, placenta, lung, liver, muscle, pancreas, spleen, thymus, prostate, ovary, intestine, colon or leukocytes. In contrast, 5-HT3A MRNA was detected only in intestine and colon, thus demonstrating that the 5-HT3A and 5-HT3B subunit genes have distinctive expression patterns. However, Northern signals are fairly weak, and it is thus possible that expression occurs below the level of detection. It is thus possible that 5-HT3A and 5-HT3B subunits could assemble in tissues where both are expressed.

EXAMPLE 3

Transient Expression of Functional 5-HT3B Receptor

The nucleotide sequence encoding the 5-HT3B protein is inserted into the expression vector pCDM8 and transfected into HEK-293 cells. The transformed cells transiently express the 5-HT3B receptor at their surfaces and are used to screen candidate agonist and antagonist compounds.

In more detail, the HEK-293 cells are transfected with pCDM8 containing the 5-HT3B protein encoding DNA by a procedure adapted from Chen, C. et al. *Mol Cell Biol* (1987) 7:2745–2752. The cells are maintained in MEM supplemented with 10% FBS, pen/strep and glutamine in 5% $CO_2$, 37° C.

The transformed colonies are then assayed for expression of the 5-HT3B receptor using the voltage clamp assay or ligand binding assay described hereinabove.

EXAMPLE 4

Stable Expression of 5-HT3B Receptor

The nucleotide sequence encoding the 5-HT3B protein of FIG. 1A or 1B is inserted into the expression vector pRC/CMV and transfected into HEK-29 cells as described by Lankiewicz et al. supra. The transfected cells express the 5-HT3B receptor at their surfaces and are used to screen candidate agonist and antagonist compounds.

In more detail, the HEK-293 cells are transfected with pRC/CMV by a procedure adapted from Chen, C. et al. supra. The cells are maintained in DMEM supplemented with 10% FBS, pen/strep and glutamine in 5% $CO_2$, 37° C.

Exponentially growing cells are removed with trypsin-EDTA and plated at a density of $1.5 \times 10^6$ cells per 10 cm plate and incubated overnight in 5% $CO_2$, 37° C. Transformed cells are selected with G418. The transformed colonies are then assayed for expression of the 5-HT3B receptor by electrophysiological and radioligand binding assays as described above.

What is claimed is:

1. A DNA molecule which comprises a recombinant expression system, which expression system comprises a nucleotide sequence encoding a protein having the activity of human 5-HT3B receptor, said protein being encoded by the nucleotide sequence set forth in FIG. 1B (SEQ. ID. NO: 1) or in FIG. 2B (SEQ. ID. NO: 3) or said protein having amino acid sequence at least 95% homologous to that encoded by SEQ. ID. NO: 1 or SEQ. ID. NO: 3, operably linked to control sequences for expression of said encoding nucleotide sequence.

2. The DNA molecule of claim 1 wherein said control sequences are heterologous to said encoding nucleotide sequence.

3. Recombinant host cells modified to contain the DNA molecule of claim 1.

4. A method to produce human 5-HT3B receptor which method comprises culturing the cells of claim 3 and recovering the receptor from the culture.

5. A human 5-HT3B receptor prepared by the method of claim 4.

6. The DNA molecule of claim 1, wherein said nucleotide sequence does not encode the signal sequence encoded by SEQ. ID. NO: 1, or SEQ. ID. NO: 3, but encodes a signal sequence heterologous thereto, whereby said signal sequence is operably linked to said protein.

7. The DNA molecule of claim 1, wherein said encoding nucleotide sequence encodes said protein having human 5-HT3B receptor activity as a fusion protein.

8. The DNA molecule of claim 1, wherein the encoded protein exhibits at least 98% amino acid identity to the protein encoded by SEQ. ID. NO: 1 or SEQ. ID. NO: 3.

9. The DNA molecule of claim 1, wherein the encoded protein exhibits at least 99% amino acid identity to the protein encoded by SEQ. ID. NO. 1 or SEQ. ID. NO: 3.

10. The DNA molecule of claim 1, wherein the encoded protein is identical to the protein encoded by SEQ. ID. NO: 1 or SEQ. ID. NO: 3.

11. A recombinant host cell modified to contain a protein having human 5-HT3B receptor activity displayed at its surface, wherein said protein has an amino acid sequence set forth in FIG. 1A (SEQ ID NO:2) or 1B (SEQ ID NO:4) or an amino acid sequence having 95% amino acid identity thereto.

12. The cell of claim 11 wherein said receptor has an amino acid sequence set forth in FIG. 1A (SEQ ID NO:2) or 2A (SEQ ID NO:4).

13. The cell of claim 11, wherein said protein has human 5-HT3B receptor activity and has 98% amino acid identity to the amino acid sequence set forth in SEQ. ID. NO: 2 or SEQ. ID. NO: 4.

14. The cell of claim 11, wherein said protein has human 5-HT3B receptor activity and has 99% amino acid identity to the amino acid sequence set forth in SEQ. ID. NO: 2 or SEQ. ID. NO: 4.

* * * * *